(12) United States Patent
Cree

(10) Patent No.: US 8,770,194 B2
(45) Date of Patent: Jul. 8, 2014

(54) GAS ASSISTED RE-BREATHING DEVICE

(75) Inventor: Robert E. Cree, Newark, NY (US)

(73) Assignee: Dive Cobalt Blue, LLC, Newark, NY (US)

( * ) Notice: Subject to any disclaimer, the term of this patent is extended or adjusted under 35 U.S.C. 154(b) by 301 days.

(21) Appl. No.: 13/016,664

(22) Filed: Jan. 28, 2011

(65) Prior Publication Data

US 2012/0192868 A1 Aug. 2, 2012

(51) Int. Cl.
*A61M 16/08* (2006.01)
*A61M 16/00* (2006.01)

(52) U.S. Cl.
CPC ....... *A61M 16/0891* (2014.02); *A61M 16/0883* (2014.02); *A61M 16/08* (2013.01)
USPC ............ 128/205.16; 128/205.17; 128/205.13; 128/205.14; 128/204.18; 128/200.24

(58) Field of Classification Search
USPC ............. 128/200.24, 201.26–201.28, 205.17, 128/205.24, 205.27, 205.28, 204.18, 128/204.28, 205.13–205.18
See application file for complete search history.

(56) References Cited

U.S. PATENT DOCUMENTS

| | | | | |
|---|---|---|---|---|
| 1,737,575 | A * | 12/1929 | Dräger | 128/203.28 |
| 3,556,095 | A * | 1/1971 | Ismach | 128/204.28 |
| 3,575,167 | A * | 4/1971 | Michielsen | 128/205.28 |
| 4,273,120 | A | 6/1981 | Oswell | |
| 4,453,543 | A * | 6/1984 | Kohnke et al. | 128/203.28 |
| 4,498,470 | A * | 2/1985 | Warncke | 128/202.26 |
| 4,567,889 | A * | 2/1986 | Lehmann | 128/204.28 |
| 4,667,669 | A * | 5/1987 | Pasternack | 128/204.23 |
| 4,781,184 | A * | 11/1988 | Fife | 128/205.12 |
| 4,811,732 | A * | 3/1989 | Hartung | 128/204.26 |
| 4,879,996 | A * | 11/1989 | Harwood, Jr. et al. | 128/202.26 |
| 4,883,051 | A * | 11/1989 | Westenskow et al. | 128/204.21 |
| 4,939,647 | A | 7/1990 | Clough et al. | |
| 4,964,404 | A | 10/1990 | Stone | |
| 4,974,585 | A | 12/1990 | Stone | |
| 4,994,117 | A | 2/1991 | Fehder | |
| 5,072,728 | A * | 12/1991 | Pasternack | 128/204.18 |

(Continued)

FOREIGN PATENT DOCUMENTS

WO 99/03524 1/1999

OTHER PUBLICATIONS

U.S. Appl. No. 13/016,673, filed Jan. 28, 2011 (26 pages).
U.S. Appl. No. 13/016,690, filed Jan. 28, 2011 (20 pages).

(Continued)

*Primary Examiner* — Annette Dixon
(74) *Attorney, Agent, or Firm* — Brian B. Shaw, Esq.; Harter Secrest & Emery LLP

(57) ABSTRACT

A gas assisted re-breathing device is provided for life support of individuals venturing into harsh environments, particularly the underwater environment, which results in reduced work of breathing. In the pressurized gas assisted re-breathing device, pressurized gas, actuated by the breathing pressure local to the mouthpiece, acts to move a flexible gas storage container on behalf of the individual and a loop seal valve is forcibly shut during assisted breathing, which seals the assisted breathing loop to prevent premature venting of breathing gas to the surrounding environment, unless the assisted breathing loop is full, whereupon the loop seal valve opens to allow excess breathing gas to escape into the surrounding environment through forcible exhalation by the individual through one or more conventional one way valves that prevent backflow from the surrounding environment back into the loop.

22 Claims, 6 Drawing Sheets

(56) References Cited

U.S. PATENT DOCUMENTS

| | | | |
|---|---|---|---|
| 5,076,267 A * | 12/1991 | Pasternack | 128/205.22 |
| 5,368,018 A | 11/1994 | Stone | |
| 5,509,406 A * | 4/1996 | Kock et al. | 128/203.14 |
| 5,678,540 A | 10/1997 | Kock et al. | |
| 5,924,418 A | 7/1999 | Lewis | |
| 6,003,513 A | 12/1999 | Readey et al. | |
| 6,349,723 B1 * | 2/2002 | Kock | 128/203.28 |
| 6,408,847 B1 | 6/2002 | Nuckols et al. | |
| 6,526,971 B2 | 3/2003 | Kellon | |
| 6,712,071 B1 | 3/2004 | Parker | |
| 6,817,359 B2 | 11/2004 | Deas et al. | |
| 2001/0015203 A1 | 8/2001 | Cumming | |
| 2010/0012124 A1 | 1/2010 | Deas | |

OTHER PUBLICATIONS

U.S. Appl. No. 09/730,628, filed Dec. 5, 2000).

* cited by examiner

GAS ASSISTED RE-BREATHING DEVICE

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A "SEQUENCE LISTING"

Not applicable.

FIELD OF THE INVENTION

A re-breathing apparatus utilizing pressurized gas to assist the breathing process resulting in reduced work of breathing is disclosed.

BACKGROUND OF THE INVENTION

For individuals venturing into underwater environments, breathable gas is typically delivered from a compressed gas storage tank and demand system known as SCUBA (Self Contained Underwater Breathing Apparatus). The most common form termed open circuit, releases pressurized gas through a regulator which contains a diaphragm located adjacent the divers mouth that senses and is responsive to the divers breathing pressure. The diaphragm acts to move a demand valve to deliver breathing gas to the diver when required and all subsequently exhaled gas typically passes back into the regulator and is directed through a one way valve into the surrounding environment where it is permanently lost for use by the diver. During inhalation, the one way valve seals the regulator off from the surrounding environment to prevent water from back flowing and choking the diver. The sensitivity of present art regulators is such that very little effort is required to inhale or exhale underwater. Since open circuit gas is used only once, divers are required to carry a large volume of pressurized gas proportional to the inhalation rate of the diver as well as to the depth the gas is breathed, which limits the amount of time a diver has available underwater to the amount of gas carried with them. As depths increase, ambient pressure increases by about 1 atmosphere for every 33 feet/10 meters. At a depth of 33 feet/10 meters, the diver is subjected to 2 atmospheres of pressure (one atmosphere at the surface plus one additional for the 33 feet/10 meters of water) and a scuba tank will last only ½ as long as it would at the surface, and at depths of 300 feet now commonly visited by divers, that same tank will last about $\frac{1}{10}$ the duration at the surface.

As time underwater and depth continue to increase, divers increase the size and quantity of tanks until the bulk and complexity are too much to handle. To deal with this issue, divers are turning to devices known as re-breathers that capture exhaled gas in one or more flexible storage container, known commonly as a counterlung, and return a portion to the diver for re-breathing. By recycling the breathed gas, re-breathers extend usable time from a given amount of gas, by as much as 20 times. To recycle exhaled gas, the re-breather must eliminate unwanted carbon dioxide (CO2) naturally introduced by the body as part of the respiration process or death can result. To do this, re-breathers process breathing gas in a loop like fashion to pass through a device known as a CO2 scrubber containing a suitable chemical agent such as lime that chemically absorbs CO2, releasing heat and water in a well understood process. As long as the scrubber is appropriately sized and designed, CO2 free gas results that is then returned back to the diver to be breathed again, forming what is known in totality as a breathing loop.

In all presently implemented systems, re-breathed gas is driven through the loop directly by the breathing pressure of the diver and present art re-breathers require more breathing effort compared to open circuit, thus it is very important to minimize flow restrictions in the breathing loop to maintain the work of breathing (WOB) to reasonable levels. The duration and CO2 removal capability of the scrubber is increased by employing larger, more complex scrubbers filled with agent made with finer sized granules that all act together to increase the total available active surface area, and unfortunately, also act to increase the WOB required in the loop. Work of breathing and scrubber duration are two of the most important performance criteria for re-breathers since it is critical to the survival of the diver that they be able to breathe easily enough to adequately ventilate the body with enough metabolic oxygen to survive as well as expel CO2 that is metabolically produced by the body. Once outside the body, CO2 must be continually and effectively removed from the breathing loop by the scrubber or an incapacitating condition known as hypercapnia can result which, although it might be survivable at the surface, can easily lead to death while underwater. It is particularly desirable to reduce the WOB of the entire rebreathing system and add safety features that would otherwise not be practical due to the associated increase in WOB such as an improved CO2 scrubber.

One idea to reduce WOB that several divers have considered and typically rejected for reasons of complexity, uses compressed gas carried by the diver to assist the counterlung in expansion and contraction during breathing such as described in U.S. published patent application No. 2001/0015203. This approach, teaches about a device that adds pressurized drive gas to a small isolated sub-section of the flexible storage container that collects exhaled breathing gas from the diver, where the added drive gas acts to assist the diver in the exhalation process. Inhalation is also assisted by bleeding off the added pressurized drive gas to allow the flexible storage container to forcibly contract. The device trades work by the diver for work by the drive gas acting on the flexible storage container to move breathing gas through the loop resulting in a reduction in WOB by the diver. The extra motive force created by the drive gas acting on the flexible storage container also creates higher pressures in the breathing loop rather than in the diver's lungs. With each breathe, the volume of added drive gas builds up and must be vented from the loop or an over pressurize condition will result. The device features one way pressure relief valves to rid the breathing loop of this excess breathing gas and exhaust it to the surrounding environment. Ideally, this exhaust would occur once the flexible storage container is fully expanded and cannot contain additional gas. In this case assisted breathing no longer will function and the diver must create the motive force to expel the excess gas. Accordingly, these one way valves must be set to open at a pressure low enough that allows the diver to comfortably expel excess breathing gas without assistance when the loop is filled to full capacity. Unfortunately, the higher loop pressures that occur during assisted breathing causes breathing gas to undesirably escape from the loop through the one way pressure relief valves set to relieve at these lower pressures and extensive testing has shown that so much breathing gas is lost as to render the concept useless. It would be extremely desirable to provide an assisted re-breathing device that does not prematurely leak breathing gas to the surrounding environment during assisted breathing which also provides for unassisted exhalation of excess breathing gas from the loop to the surrounding environment by the diver with a lower breathing pressure similar to open circuit scuba.

In prior art re-breathers, additional one way valves are used to ensure un-scrubbed exhale gas laden with CO2 is not re-breathed and is instead directed to pass properly through the scrubber. These valves are typically located as close to the mouth as possible to minimize the volume of gas that can be directly re-inhaled, one positioned to allow exhaled gas to pass down into the re-breather for temporary storage and scrubbing and a separate one turned in the opposite direction to receive scrubbed gas back from the re-breather and pass it back to the diver for inhalation. Most one way valves are designed as simple flexible membranes that under reverse flow conditions, normally act to effectively seal off flow passages and open only under forward flow conditions to allow flow to move in the proper direction around the loop. These one way valves resist the flow of breathing gas and add to the WOB, increasing resistance with increased breathing gas flow. To reduce WOB, a minimum number of one way valves are used and their size is maximized. Many accidents have been reported involving the failure of one way valves that allowed exhaled gas to be directly re-inhaled, leading to buildup of CO2 in the loop. It is highly desired to maintain loop flow direction integrity when failure of a one way check valve occurs.

Particularly insidious is that hypercapnia can arise quite rapidly. A condition commonly known as breakthrough occurs when the scrubbing agent is depleted in any location enough to allow a significant portion of CO2 to pass through the scrubber, rendering it unusable. It is well understood that heavy breathing and/or deeper depths cause CO2 to pass further through the scrubber which can lead to early breakthrough. Breakthrough can also occur due to improper packing of the agent into the scrubber with a condition known as channeling, where re-breathed gas follows a low resistance to gas flow path that quickly depletes the locally surrounding scrubbing agent and allows CO2 to prematurely channel through the scrubbing bed. Warning systems for the presence of CO2 have only recently been introduced with limited success due to extreme sensitivity exhibited by available sensors to high relative humidity environments such as what exists naturally in a re-breather loop. Prior art systems that do exist, employ barriers made of sponges and/or water impermeable membranes placed between the loop and the sensor to limit water intrusion, which unfortunately also degrades the response time of the sensor, making it relatively ineffective when CO2 rapidly builds up, or worse, can render the sensor useless if water saturation of the barrier occurs. Instead, most divers today rely on indirect measurements such as the time a scrubbing agent bed has been in service versus conservative experience as well as the direct measurement of scrubber temperature to determine when to stop using the bed. Since the scrubbing process naturally generates heat, a temperature rise indicates the agent is being activated by the presence of CO2 and when this occurs near the end of the bed, it is time to stop using the re-breather. Unfortunately, CO2 breakthrough tends to occur quite suddenly, especially during periods of heavy exertion and/or at deeper depths, making predictions based on time and temperature quite fallible. Due to significant safety concerns, re-breather divers would like to quickly and reliably monitor for the life threatening presence of CO2 in the loop, especially at higher work levels and/or deeper depths when a rapid buildup can occur without warning.

Re-breathers also must provide make up for oxygen absorbed from inhaled gas by the body to satisfy the metabolic needs of the diver. It is well understood that at constant workload, the rate of metabolic oxygen consumption is more or less constant, requiring roughly the same number of O2 molecules per unit time, meaning oxygen consumption is proportional to mass flow. Additionally, it is well known that metabolism and associated oxygen consumption by the divers body, changes more or less proportional to workload and respiration rate, therefore the harder you work, the higher the respiration rate, and the larger the mass flow requirement for metabolic makeup oxygen. Similar to open circuit gas consumed with depth, if a fixed mass sample of oxygen were isolated in a flexible container at the surface, it would shrink to ½ the volume at 33 feet and ¹/₁₀th the volume at 300 feet, yet this fixed mass would sustain the diver for the same period of time metabolically. Overall, metabolic consumption requires makeup oxygen volumetric flow to increase proportional to respiration rate and drop inversely proportional to depth induced pressure.

In diving operations, the amount of oxygen present in the breathing gas is measured in terms of oxygen partial pressure or PO2, usually expressed in standard atmospheres of pressure. Normal oxygen at the surface is 21% of one atmosphere and is expressed as 0.21 PO2, whereas 100% pure oxygen at the surface is 1.00 PO2. It is well recognized that for safe diving operations, the oxygen content of breathing gas should always remain in the range of about 0.16<PO2<1.60. Too little oxygen, known as hypoxia, is a deadly condition that occurs below around 0.16 PO2, where insufficient oxygen is present to sustain life. Too much oxygen, termed hyperoxia, becomes toxic over time to the central nervous system (CNS). Commonly referred to by divers as CNS toxicity, high oxygen levels eventually lead to uncontrolled convulsions, which when convulsions occur underwater, place the diver at extreme risk of death due to drowning. Typically this condition strikes without warning, and evidence supports that toxicity is accelerated by elevated CO2 levels. Several prior art methods are used in re-breathers, that attempt to maintain safe levels of oxygen in the breathing loop.

One method, such as employed in U.S. Pat. No. 6,526,971 and present art rebreathers known as the RB80, forcibly eject a portion of the exhaled gas from the loop that is replaced by passive addition of a gas mix containing some amount of oxygen, linked to the respiration rate of the diver. Oxygen levels in the loop drop and stabilize to several percent below injected levels. Divers must be very careful not to allow hypoxia to set in, especially at shallower depths where the percent drop is amplified. Another method allows the diver to manually actuate a valve to add oxygen to the loop as required. Yet another method bleeds oxygen into the loop using a fixed orifice driven by a special regulator designed to maintain a constant, absolute pressure on one side of the orifice, with ambient pressure on the other, with enough differential pressure to cause sonic flow through the orifice. As ambient pressure increases with depth, pressure across the orifice drops, producing a roughly constant mass flow of oxygen as depth changes in a well understood process that is not linked to the respiration rate of the diver. As ambient pressure increases sufficiently to cause the orifice to drop into sub-sonic operation, mass flow is reduced, ultimately to zero when ambient pressure equals the set pressure of the absolute pressure regulator. In these systems, the diver normally chooses an orifice sized to produce flow somewhat below their resting metabolic rate such that an occasional manual add of oxygen is required to make up for any shortfall and more frequent additions are required at deeper depths when the orifice goes sub-sonic and with increased workloads. It is very important in these systems that the diver closely monitor oxygen content within the breathing loop so that timely additions can be made to remain safe. Another system automatically monitors and controls oxygen addition using an electronic closed loop computer control system that periodically cycles an electric oxygen addition valve to maintain oxygen levels within the loop. Electronic systems are susceptible to failure in underwater environments and it is very important that oxygen monitoring sensors be accurate to facilitate safe operation of re-breathers employing them.

Prior art oxygen monitoring within the re-breathing loop is commonly accomplished using some form of galvanic sensor which unfortunately, are proven in practice to not be all that reliable. Sensors typically exhibit a relatively short life expectancy of just several months to a year or two, are also susceptible to malfunction when exposed to condensing water and provide little warning they are about to fail. When they do wear out or fail, they report oxygen levels different from what is actually present. Due to reliability concerns, divers typically employ multiple sensors, sequence them in age, and even employ sophisticated real time computer algorithms to determine the health and believability of sensors. In the end, sensor health is left up to the diver to evaluate and this requires constant vigilance to remain safe. It is particularly desirable to eliminate the need for electronic controls and sensor feedback to properly add and maintain oxygen levels in underwater re-breathing devices.

BRIEF SUMMARY OF THE INVENTION

A gas assisted re-breathing device with a loop seal valve that prevents premature venting of breathing gas, which results in reduced work of breathing and further facilitates the introduction of features not presently feasible due to associated increases in work of breathing. The gas assisted re-breathing device comprises at least one flexible gas storage container in an assisted breathing loop, driven by pressurized gas, which in underwater applications, is normally carried by the diver. Pressurized gas is actuated by the breathing pressure local to the divers mouth, acting to move the flexible gas storage container on behalf of the diver to significantly reduce work of breathing, and a loop seal valve that acts to seal the assisted breathing loop to prevent premature venting of breathing gas to the surrounding environment, unless the assisted breathing loop is full, whereupon the loop seal valve opens to allow excess breathing gas to be forcibly exhaled by the divers breathing pressure out into the surrounding environment through one or more conventional one way valves, preventing backflow from the surrounding environment back into the loop. The loop seal valve is preferentially actuated by pressurized drive gas that also acts on the flexible gas storage container. Spent pressurized drive gas is preferentially released inside the assisted breathing loop of the re-breathing apparatus for use by the re-breathing individual.

Further disclosed is a method to utilize this cyclic pressurized drive gas to actuate metabolic makeup gas addition without the use of electronics, in the proper proportions necessary to support the diver's metabolism as described in co-pending application concurrently filed with this application entitled CONSTANT MASS OXYGEN ADDITION INDEPENDENT OF AMBIENT PRESSURE, filed Jan. 28, 2011 and assigned application Ser. No. 13/016,673, by the same inventor as the present application and herein incorporated by reference. Also disclosed is one implementation of CO2 detection using the reduced relative humidity CO2 detection device described in co-pending application concurrently filed with this application entitled CO2 MEASUREMENT IN HIGH RELATIVE HUMIDITY ENVIRONMENTS, filed Jan. 28, 2011 and assigned application Ser. No. 13/016,690, by the same inventor as the present application and herein incorporated by reference. Additionally disclosed is the rapid and easy switchover from re-breathing to open circuit breathing, easy adjustment of decompression gases up to 100% oxygen, redundant one way valves to control the flow of breathing gas in the loop, bigger and more complex CO2 scrubbers for better performance, and a reciprocating water removal pump.

Other features and advantages will become apparent from the following detailed description, the drawings, and the claims.

DETAILED DESCRIPTION OF THE INVENTION

Figure 1:
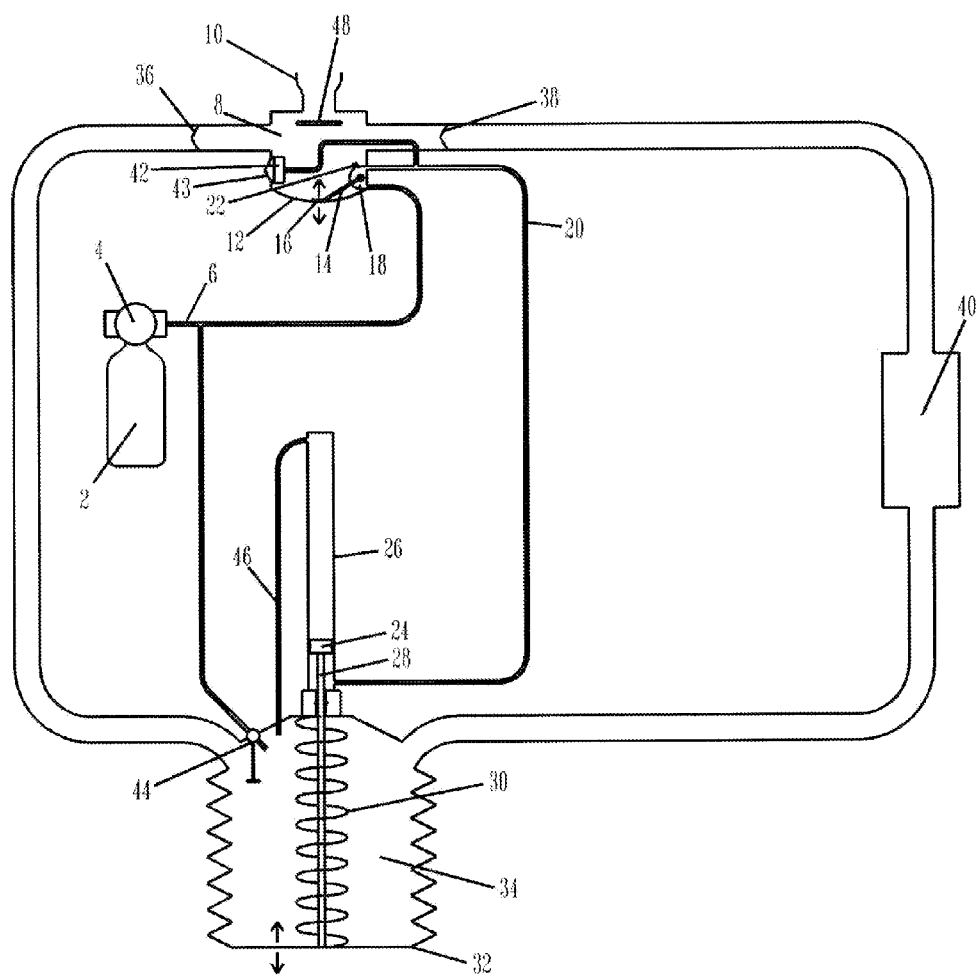
FIG. 1 is a schematic view of a gas assisted re-breathing device with a loop seal valve and spring return according to a preferred embodiment.

Referring to FIG. 1, according to a preferred embodiment, high pressure gas storage bottle 2 containing a pressurized gas source with attached high pressure regulator 4, delivers pressurized gas through connecting hose 6 to breathing regulator 8. High pressure regulator 4 is of the well known scuba design, which maintains a constant pressure above the surroundings. Breathing regulator 8 is sealed internally or externally to the mouth of a diver using mouthpiece 10, which allows the diver to breath in and out of breathing regulator 8 such that the divers breathing pressure acts on flexible diaphragm 12. Flexible diaphragm 12 moves inward when the diver inhales and outward when exhaling, acting to move actuator lever 14 in and out, which is loosely held attached to diaphragm 12 by retaining loop 16. Actuator lever 14, responsive to inhale and exhale pressure from the diver, acts on diver inhale to move low pressure regulator valve 18 to direct pressurized gas from connecting hose 6 to drive gas delivery tube 20, or on exhale, to direct gas from drive gas delivery tube 20 to regulator valve vent 22 causing a pressurized drive gas to form inside drive gas delivery tube 20 that is variable in pressure, responsive to inhale and exhale breathing pressure from the diver, such that pressurized drive gas increases in pressure during inhalation and decreases in pressure during exhalation.

On diver inhalation, low pressure regulator valve 18 directs pressurized drive gas from connecting hose 6 through gas delivery tube 20 which is applied to the drive side of drive piston 24 that is sealed and slides inside drive cylinder 26 applying a moving force to drive shaft 28 to compress drive spring 30 forming one possible configuration of a positioning system that acts on flexible (variable volume) container 32 to compress the volume of variable volume gas space 34. Drive tube vent 46 prevents a pressure buildup on the non-drive side of drive piston 24 ensuring free motion within drive cylinder 26. One way exhale valve 36 allows exhaled breathing gas from the diver to flow only from breathing regulator 8 into variable volume gas space 34, but not in reverse, and similarly one way inhale valve 38 allows inhaled breathing gas to flow only from variable volume gas space 34 through CO2 scrubber 40 into breathing regulator 8. Together, one way exhale valve 36 and one way inhale valve 38 act to direct breathing gas emanating from variable volume gas space 34 to forcibly and on demand by the diver, flow through CO2 scrubber 40 and breathing regulator 8 to be inhaled by the diver. CO2 scrubber 40 acts to remove deadly CO2 from exhaled breathing gas in a well understood and implemented process.

On diver exhalation, low pressure regulator valve 18 vents pressurized drive gas applied during the inhalation cycle to the drive side of drive piston 24, back through drive gas delivery tube 20 and out through regulator valve vent 22 into breathing regulator 8 where it is added to the breathing gas exhaled by the diver. Drive spring 30 acts against now venting (reducing) pressure applied to drive piston 24, which allows drive spring 30 to expand and the positioning system now acts on flexible container 32 to forcibly expand and draw breathing gas into variable volume gas space 34. Together, one way exhale valve 36 and one way inhale valve 38 both act to direct diver exhaled breathing gas and vented drive gas from regulator vent valve 22 to flow on demand by the diver directly into the now forcibly expanding variable volume gas space 34 ready for breathing by the diver.

During the exhale and inhale cycles, breathing gas travels generally sequentially through all connected components in a loop like fashion, forming a breathing loop that acts to recycle breathing gas back to the diver inside what is known generically as a re-breathing device. The breathing loop includes all components of the re-breathing device that come into contact with breathing gas. An assisted breathing loop is formed when the re-breathing device includes any form of positioning system that is responsive to the breathing pattern of the user acting to forcibly position flexible container 32 and move breathing gas around the loop on behalf of the user. In this preferred embodiment, breathing gas enters the assisted breathing loop from the diver during exhalation through mouthpiece 10 into breathing regulator 8, passing sequentially through several major components that act to define loop like flow for a major portion of the breathing gas, first through one way exhale valve 36 and into flexible container 32 that is under positioning system control responsive to the breathing pattern of the user, where it accumulates for re-breathing. On inhalation, with continued responsiveness to the breathing pattern of the user, the positioning system now forcibly causes breathing gas to pass out of flexible container 32, through CO2 scrubber 40, one way inhale valve 38, and back into breathing regulator 8 where it is inhaled by the diver through mouthpiece 10. Breathing loop components are directly connected to one another or connected by some form of conduit such as flexible hose material, forming an enclosed space with a volume that varies, primarily dependent on the expansion and contraction of connected component, flexible container 32. The total connected volume at any given time is collectively known as the assisted breathing loop volume or simply the loop volume when a positioning system is not present.

Alternately, and not shown, CO2 scrubber 40 can be positioned on the opposite side of flexible container 32 within the loop such that diver exhaled breathing gas and vented drive gas from regulator vent valve 22 flow through CO2 scrubber 40 prior to entering flexible container 32. Further, more than one flexible container 32 and/or CO2 scrubber 40 can be used and the order within the loop is not critical.

Loop volume changes occur over time for several reasons such as a build up of vented drive gas, changes in diver depth and changes in diver work load. When insufficient breathing gas is present in the loop, flexible container 32 compresses to near its minimum volume limit where it presses against loop volume makeup valve 44, which opens to deliver pressurized makeup gas through connecting hose 6 into variable volume gas space 34 until makeup gas is no longer required. When excess breathing gas is present in the loop, it is releasable to the surrounding environment through pressure actuated loop seal valve 42 and one way purge valve 43. During diver inhalation, pressurized drive gas in gas delivery tube 20 builds up and acts to close pressure actuated loop seal valve 42, preventing breathing gas from prematurely escaping from the assisted breathing loop into the surrounding environment. During diver exhalation, this built up pressurized drive gas continues to keep pressure actuated loop seal valve 42 closed until gas delivery tube 20 is sufficiently vented and drive gas pressure is low enough that flexible container 32 reaches its maximum volume limit and is no longer able to forcibly expand to collect exhaled breathing gas, whereupon pressure actuated loop seal valve 42 opens and allows excess breathing gas to escape into the surrounding environment through a one way purge valve 43 that also acts to prevent backflow, completing the breathing cycle. One way purge valve 43 is preferably similar to a prior art, conventional open circuit regulator one way valve, to ensure low backpressure, since excess breathing gas must now be expelled into the surrounding environment by the breathing pressure of the diver.

Mouthpiece shutoff 48 is provided to seal off mouthpiece 10 from the surrounding environment to prevent back flooding of the loop when the normal seal is broken between the diver's mouth and mouthpiece 10. If changes in loop volume occur when mouthpiece shutoff 48 is shut, the system continues to function normally to add and vent gas due to loop pressure acting directly on flexible diaphragm 12.

Figure 2A:
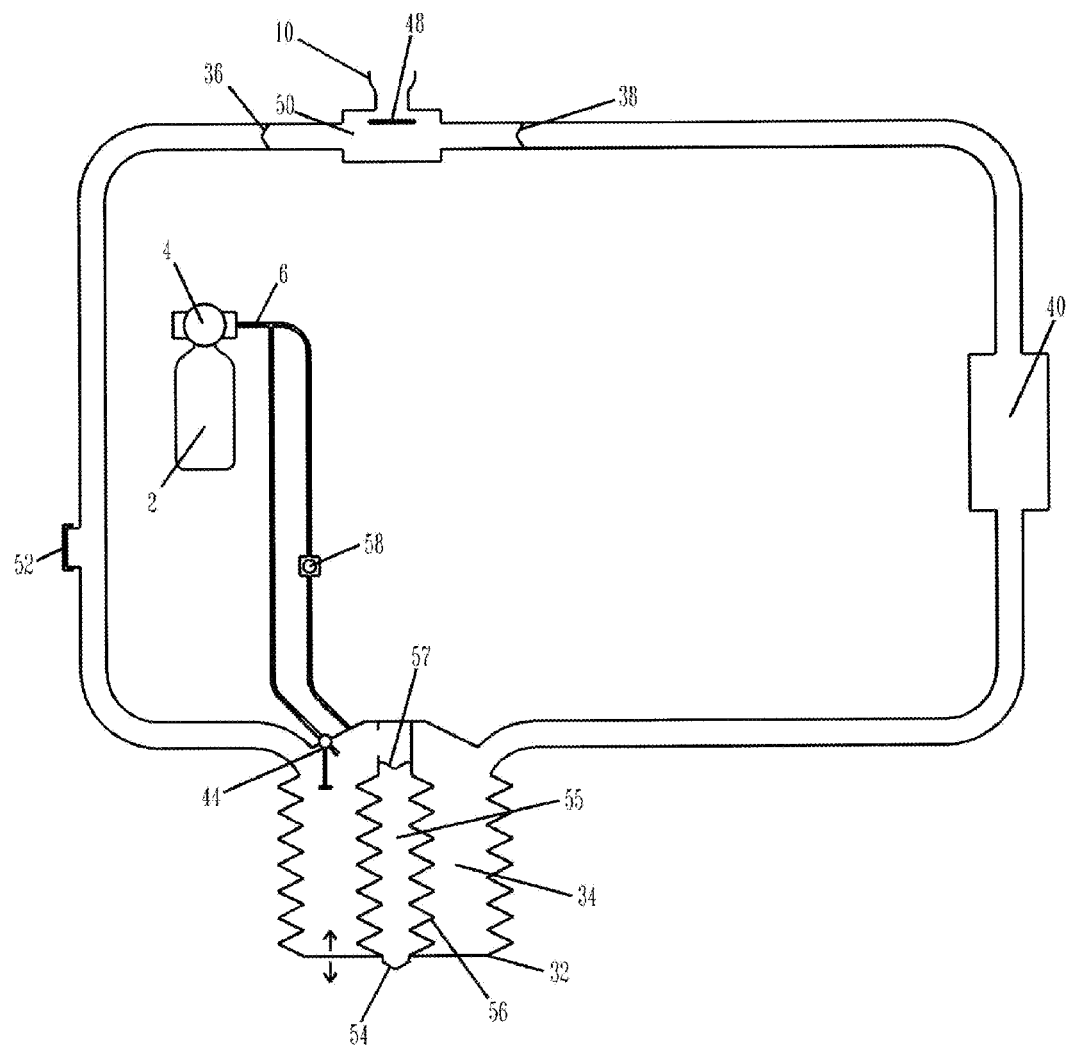
FIG. 2a is a schematic view of a prior art re-breathing device with purposeful dumping and subsequent replacement of breathing gas to provide for the metabolic oxygen needs of the diver.

Referring to FIG. 2a, in contrast and according to prior art commonly in use today, shown is a re-breathing device with a mouthpiece body 50 that is sealed internally or externally to the mouth of a diver using mouthpiece 10 which allows the diver to breath in and out of mouthpiece body 50 such that the divers breathing pressure acts directly to move breathing gas around the breathing loop without assistance from pressurized gas sources, forming an unassisted breathing loop.

On diver inhalation, negative breathing pressure acts directly on flexible container 32 to reduce the volume of variable volume gas space 34. One way exhaust valve 36 allows exhaled breathing gas from the diver to flow only from mouthpiece body 50 into variable volume gas space 34, but not in reverse, and similarly one way inhale valve 38 allows inhaled breathing gas to flow only from variable volume gas space 34 through CO2 scrubber 40 into mouthpiece body 50. Together, one way exhale valve 36 and one way inhale valve 38 act to direct breathing gas pulled by the diver from variable volume gas space 34 to flow through CO2 scrubber 40 and mouthpiece body 50 to be inhaled by the diver. CO2 scrubber 40 acts to remove deadly CO2 from exhaled breathing gas in a well understood and implemented process. On diver exhalation, positive breathing pressure acts directly to expand the volume of variable volume gas space 34. Together, one way exhale valve 36 and one way inhale valve 38 both act to direct diver exhaled breathing gas back directly into variable volume gas space 34, completing the breathing cycle. The order and quantity of CO2 scrubber(s) 40 and flexible container(s) 32 within the loop is not critical and differing arrangements exist.

Changes in total loop volume occur due to changes in diver depth, work load of the diver, and gas dumped during the breathing cycle. Any excess gas is vented into the surrounding environment through overpressure vent valve 52, preventing a system rupture from occurring. High pressure gas storage bottle 2 with attached high pressure regulator 4, delivers pressurized makeup gas through connecting hose 6 into the loop when flexible container 32 compresses to near its limit and opens loop volume makeup valve 44 or through manual addition valve 58 actuated directly by the diver. Mouthpiece shutoff 48 is provided to seal off mouthpiece 10 from the surrounding environment to prevent back flooding of the loop when the seal is broken between the diver's mouth and mouthpiece 10.

In this prior art approach, oxygen metabolized by the diver is made up by dumping a portion of breathing gas to the surrounding environment which then is replaced with fresh breathing gas. During inhalation, as the volume of variable volume gas space 34 is reduced, one way dump valve 54 allows trapped gas volume 55 contained within inner flexible container 56 to dump into the surrounding environment while one way fill valve 57 prevents backflow into variable volume gas space 34. Gas dumped from trapped gas volume 55 is made up during the inhalation cycle with makeup gas containing sufficient oxygen content to replace oxygen metabolized by the diver. During exhalation, as the volume of variable volume gas space 34 expands, one way fill valve 57 allows a portion of breathing gas to pass and fill trapped gas volume 55 while one way dump valve 54 prevents backflow from the surrounding environment into variable volume gas space 34, completing the oxygen makeup cycle.

Figure 2B:
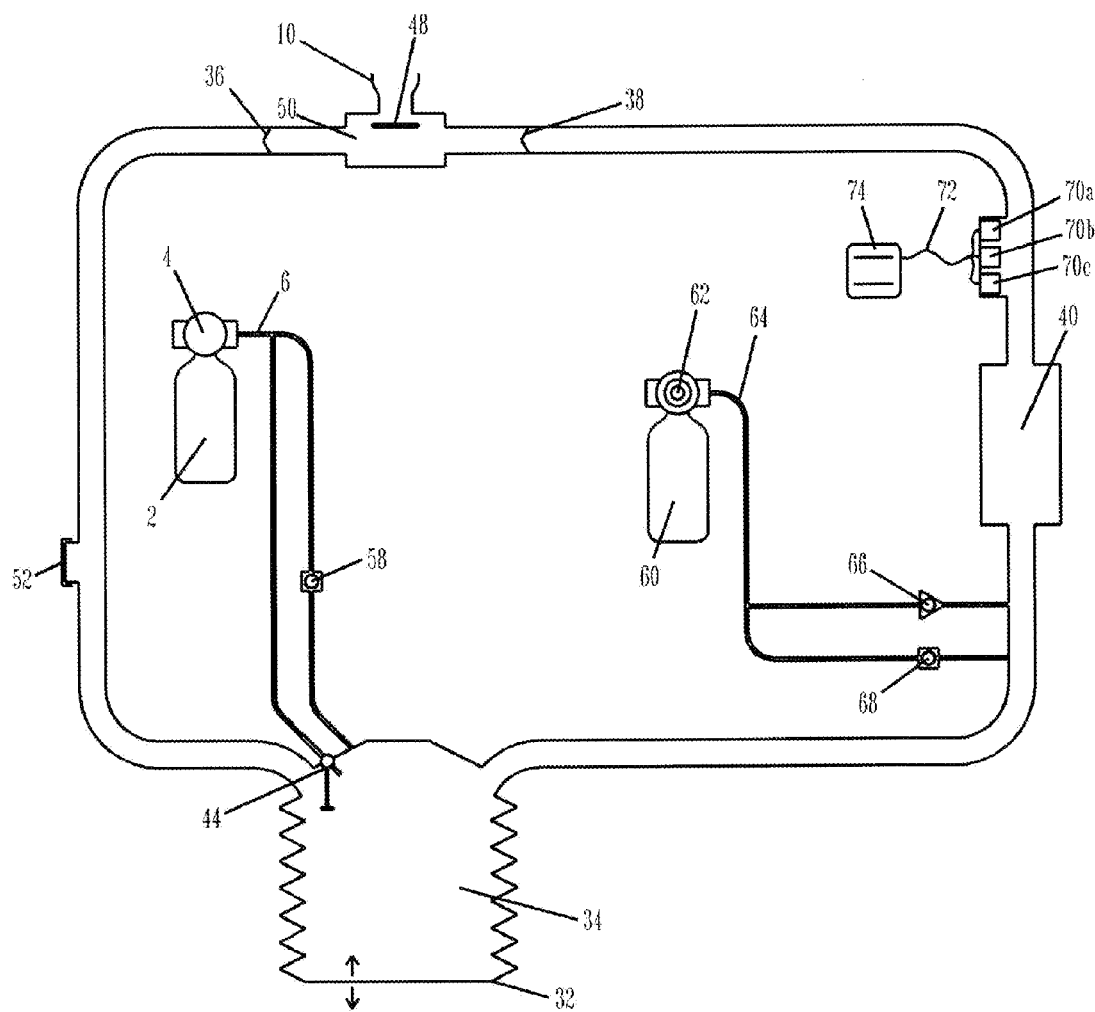
FIG. 2b is a schematic view of a prior art re-breathing device with constant bleed addition of oxygenated makeup gas to provide for the metabolic oxygen needs of the diver.

Referring now to FIG. 2b, according to prior art, this re-breathing system functions the same as in the prior art system of FIG. 2a except for the method used to make up for the metabolic oxygen use by the diver. Here, high pressure metabolic gas storage bottle 60 containing gas suitable for providing for the metabolic oxygen makeup needs of the diver, commonly pure oxygen, with attached constant pressure regulator 62, delivers pressurized metabolic makeup gas through metabolic gas connecting hose 64 to metabolic gas flow orifice 66 and metabolic gas manual addition valve 68. Constant pressure regulator 62 is of a well known present art scuba design which has been modified to maintain a fixed output pressure independent of the pressure of the surroundings which together with metabolic gas flow orifice 66 delivers metabolic makeup gas at a constant mass flow rate typically just below the metabolic needs of the diver until depth increases enough to cause metabolic makeup gas flow to stop according to well understood and implemented principles. Oxygen sensing cells 70a, 70b and 70c directly sense the amount of oxygen present in the breathing gas and electrically connect through oxygen sensor cabling 72 to dive computer 74. As one of its functions, dive computer 74 displays current oxygen levels and the diver uses metabolic gas manual addition valve 68 to fine tune metabolic makeup gas requirements to meet the metabolic needs of the diver.

Figure 2C:
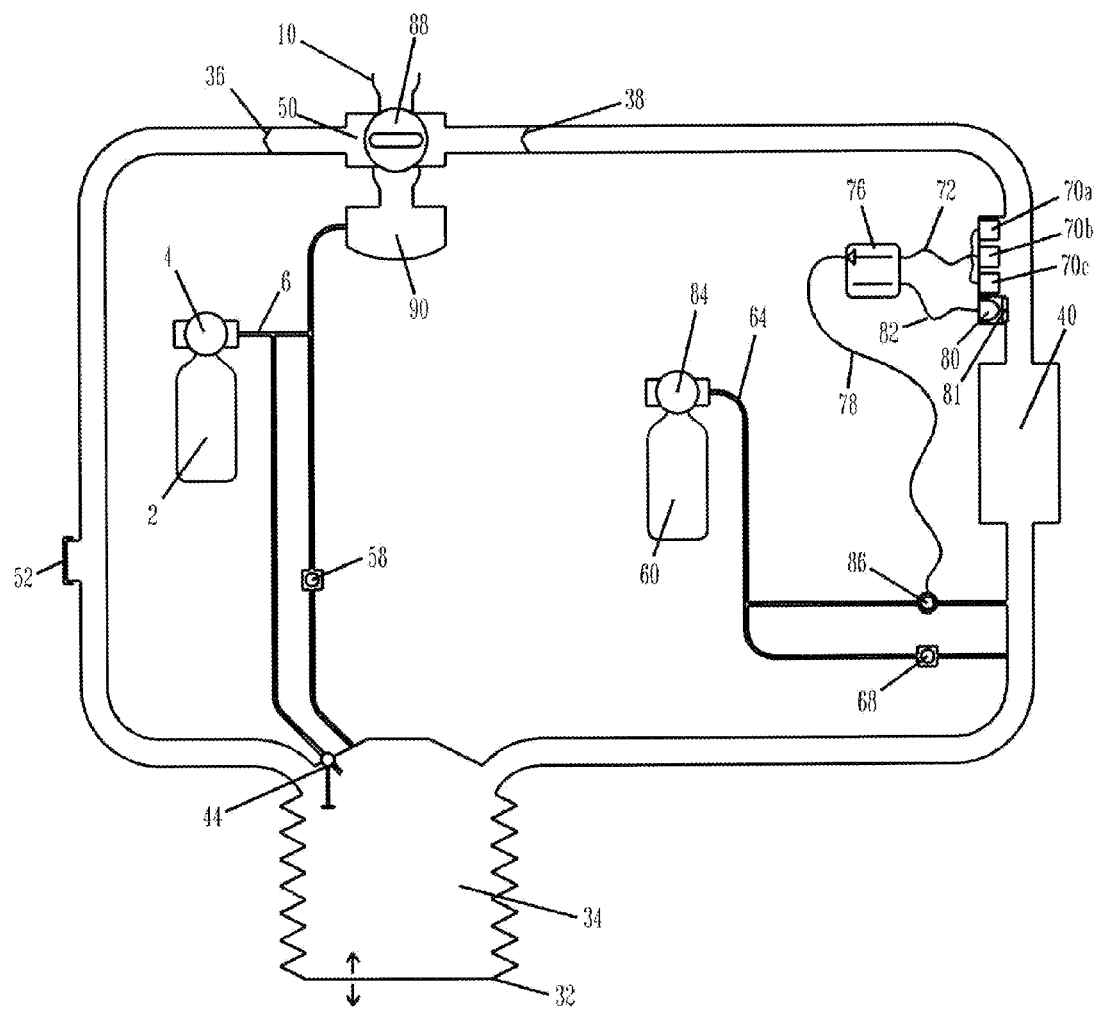
FIG. 2c is a schematic view of a prior art re-breathing device with automatic computer controlled addition of oxygenated makeup gas to provide for the metabolic oxygen needs of the diver.

Now referring now to FIG. 2c, according to prior art, this re-breathing system functions the same as in the prior art system of FIGS. 2a and 2b except for the method used to make up for the metabolic oxygen use by the diver and also shows the addition of CO2 sensor 80 for monitoring purposes and a standard scuba regulator 90 for emergency gas needs. High pressure metabolic gas storage bottle 60 containing gas suitable for providing for the metabolic oxygen makeup needs of the diver, with attached metabolic gas pressure regulator 84, delivers pressurized metabolic makeup gas through metabolic gas connecting hose 64 to metabolic gas solenoid valve 86 and metabolic gas manual addition valve 68. Metabolic gas pressure regulator 84 is of the well known prior art scuba design, which maintains a constant pressure above the surroundings. Oxygen sensing cells 70a, 70b and 70c directly sense the amount of oxygen present in the breathing gas and electrically connect through oxygen sensor cabling 72 to dive controller 76, which functions to display current oxygen levels and automatically control oxygen levels to a diver selected set point. Dive controller 76 is connected to metabolic gas solenoid valve 86 through control cable 78 and acts to open and close metabolic gas solenoid valve 86 when required to automatically maintain oxygen levels near the diver selected set point. The diver may use metabolic gas manual addition valve 68 to fine tune metabolic makeup gas requirements to meet the metabolic needs of the diver. Further, CO2 sensor 80 is connected to dive controller 76 via CO2 cable 82 and also provides for monitoring of deadly CO2 gas that might not be removed by CO2 scrubber 40 due to failure. Water barrier 81 covers CO2 sensor 80 in an attempt to limit liquid and vapor phase water from reaching CO2 sensor 80, which would render it useless.

Standard scuba regulator 90 attaches and is sealed to mouthpiece body 50. Emergency selector valve 88 is integrated within mouthpiece body 50 and allows the diver to select normal re-breather operation with the standard scuba regulator 90 isolated or to select the standard scuba regulator 90 with the re-breather isolated without having to remove the mouth of the diver from mouthpiece 10. This is optional equipment and is used in an emergency situation by re-breather divers that choose to have them. High pressure gas storage bottle 2 with attached high pressure regulator 4 delivers pressurized gas to standard scuba regulator 90, however it can alternatively be supplied from any convenient external source according diver needs.

Figure 3:
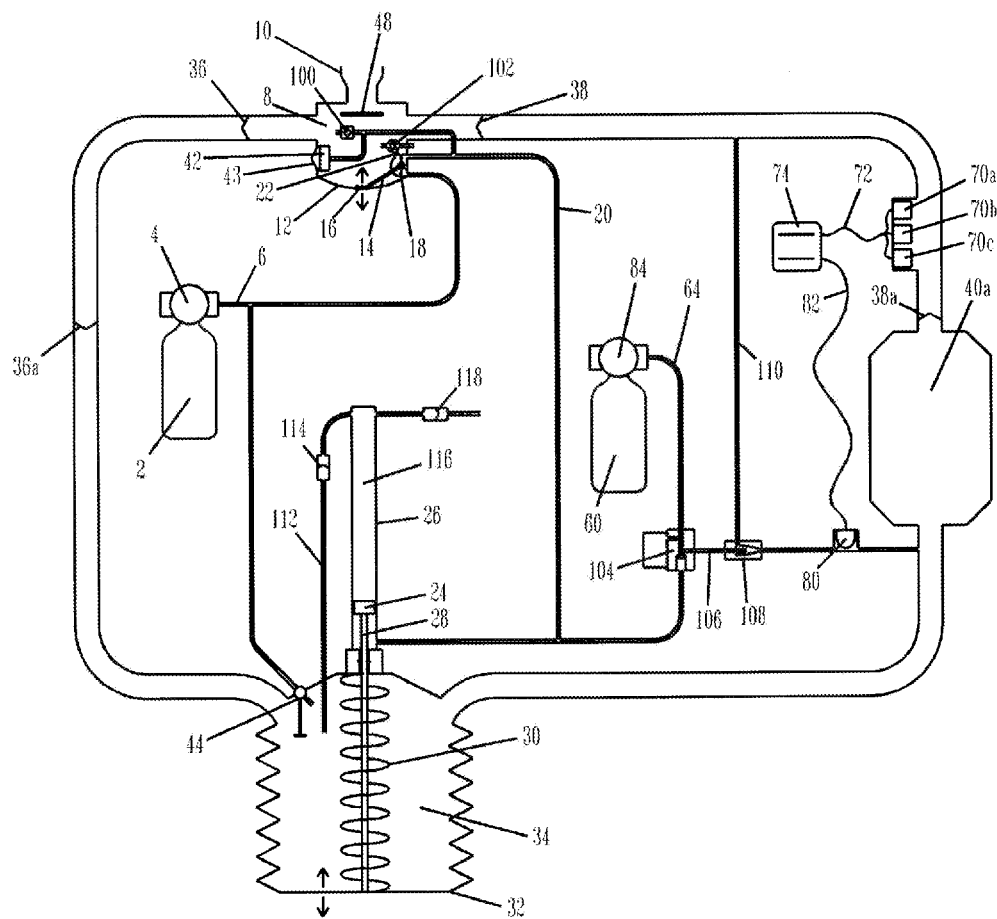
FIG. 3 is a schematic view of a gas assisted re-breathing device according to the preferred embodiment of FIG. 1 with several features facilitated by the reduced work of breathing including a pneumatically driven, respiratory linked, metabolic oxygen makeup system and a reduced relative humidity CO2 monitoring system.

Referring now to FIG. 3, this re-breathing system functions the same as in FIG. 1, with several enhancements shown, which can independently be added.

One way exhaust valve 36 and one way inhale valve 38 are exposed to the inherent probability of failure common to one way valves. Reduced work of breathing by the use of pressurized drive gas allows the addition of one way exhale backup valve 36a and one way inhale backup valve 38a. One way exhaust valve 36 and one way exhale backup valve 36a are placed in series, which is not practical due to work of breathing concerns in prior art systems, and perform the same function which drops the functional probability of failure by the square of the probability of failure for one valve only, thereby increasing reliability of the system. Similarly, for one way exhaust valve 38 and one way exhaust backup valve 38a.

Reduced work of breathing by the use of pressurized drive gas also allows for a larger and more complex CO2 scrubber 40a. Additionally, finer CO2 absorbent material can be used which is well know to last longer due to larger absorbent surface area, either inside the normal CO2 scrubber 40 of FIG. 1 or the larger and more complex CO2 scrubber 40a of FIG. 3.

Bailout slide valve 100 functionally replaces present art emergency selector valve 88 of FIG. 2c and standard scuba regulator 90 also of FIG. 2c. When bailout slide valve 100 is closed, pressurized drive gas in drive gas delivery tube 20 functions normally to change the volume of variable volume gas space 34 as described in FIG. 1. When bailout slide valve 100 is opened, pressurized drive gas in drive gas delivery tube 20 is vented inside breathing regulator 8 and allows the diver to breathe fresh gas directly from high pressure gas storage bottle 2 the same as breathing from standard scuba regulator 90 also of FIG. 2c, also known as open circuit. Since drive gas delivery tube 20 is now continuously vented through bailout slide valve 100, variable volume gas space 34 fully expands and comes to rest, drawing in fresh gas as required until it reaches and remains at its maximum volume, turning the previously assisted breathing loop into a non-assisted breathing loop. Bailout slide valve 100 can preferably be designed to operate with a quick slap of the divers hand which makes the change from re-breather to open circuit respiration much easier than the twisting motion required by present art emergency selector valve 88 of FIG. 2c and allows it to perform the dual function of purging the re-breather with fresh breathing gas if bailout slide valve 100 is opened when variable volume gas space 34 is compressed since it will expand to its maximum volume and draw in fresh gas. In case of diver incapacitation, emergency gas switches to open circuit can be performed by other divers if required.

Decompression valve 102 adjusts the portion of pressurized drive gas vented through regulator valve vent 22 into either breathing regulator 8 or out into the surroundings and has no analog in prior art systems. During normal re-breather operations described in FIG. 1, pressurized drive gas is fully vented into breathing regulator 8. At the conclusion of longer and deeper dives, it is well understood that higher levels of oxygen in the breathing gas are desired to speed the process of decompression while the diver returns to the surface. During decompression, decompression valve 102 can be adjusted by the diver to shift any portion, or all of the pressurized drive gas, which is typically low in content of oxygen, to be vented into the surroundings where it will not dilute higher oxygen levels that are desired in the breathing gas loop.

High pressure metabolic gas storage bottle 60 containing gas suitable for providing for the metabolic oxygen makeup needs of the diver, with attached metabolic gas pressure regulator 84, delivers pressurized metabolic makeup gas through metabolic gas connecting hose 64 to properoxic dosing unit 104. Metabolic gas pressure regulator 84 is of the well known present art scuba design which maintains a constant pressure above the surroundings. Pressurized drive gas in drive gas delivery tube 20 functions to actuate properoxic dosing unit 104 during each breathing cycle by the diver delivering dosed metabolic makeup gas through properoxic delivery tube 106 to the diver according to co-pending application concurrently filed with this application entitled CONSTANT MASS OXYGEN ADDITION INDEPENDENT OF AMBIENT PRESSURE, filed Jan. 28, 2011 and assigned application Ser. No. 13/016,673, by the same inventor as the present application and herein incorporated by reference. Properoxic delivery tube 106 can optionally be connected directly to the assisted breathing loop and on to the diver or can first pass through relative humidity reducer 108 as shown.

Dosed metabolic makeup gas is fed through properoxic delivery tube 106 to relative humidity reducer 108 which acts to draw breathing gas through sample tube 110 and mix with dry dosed metabolic makeup gas to reduce the combined relative humidity well below the maximum allowed for all commonly available CO2 sensors to function properly according to co-pending application concurrently filed with this application entitled CO2 MEASUREMENT IN HIGH RELATIVE HUMIDITY ENVIRONMENTS, filed Jan. 28, 2011 and assigned application Ser. No. 13/016,690, by the same inventor as the present application and herein incorporated by reference.

Mixed sample gas from relative humidity reducer 108 passes CO2 sensor 80 and enters the assisted breathing loop and on to the diver. CO2 sensor 80 is connected to dive computer 74 for processing and presentation of CO2 levels to the diver. Alternatively, any source of pressurized gas such as pressurized drive gas can be used in place of dosed metabolic makeup gas to feed relative humidity reducer 108 especially in cases when properoxic dosing unit 104 is not used.

Suction tube 112 replaces drive tube vent 46 of FIG. 1 and conducts gas or liquid present at the inlet of suction tube 112 through one way suction valve 114 and into pump space 116 located on the unpressurized side of drive piston 24 during the exhale cycle as pressurized drive gas is vented from the drive side of drive piston 24 as described in FIG. 1. During the inhale cycle, liquid and gas are expelled from pump space 116 through one way discharge valve 118 into the surrounding environment thus expelling unwanted water from the assisted breathing loop.

Figure 4:
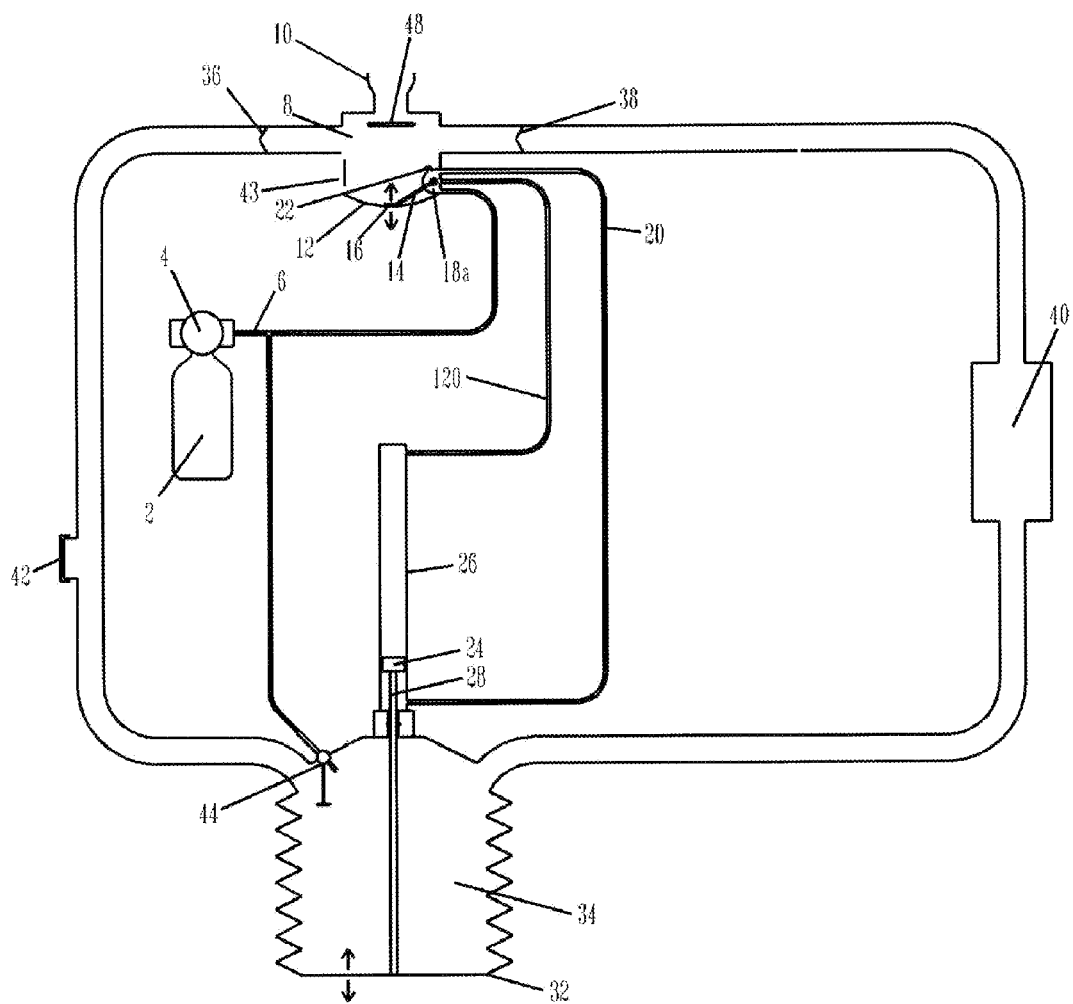
FIG. 4 is a schematic view of a gas assisted re-breathing device according to the preferred embodiment of FIG. 1 with an alternative connection between the variable volume chamber and the low pressure regulator.

Referring to FIG. 4, drive cylinder vent line 120 can connect drive cylinder 26 to the breathing regulator 8 at low pressure regulating valve 18a to prevent pressure build up on the non-drive side of the drive piston 24.

It is understood that there are many variations to the prior art systems of FIGS. 2a, 2b, and 2c and that these represent the basic principles of commonly available systems for comparative purposes. Further, it is understood that all known prior art oxygen addition and CO2 detection methods can be implemented in each of the various possible embodiments. It is further understood these embodiments also apply to other harsh environment applications such as aeronautic, medical or fire-fighting and is not limited in application strictly to the diving environment.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A re-breathing device for providing breathing gas to a user, the device comprising:
   (a) a pressurized gas source supplying a pressurized gas;
   (b) a mouthpiece providing an interface between the user and an assisted breathing loop;
   (c) a breathing regulator in the assisted breathing loop, the breathing regulator fluidly connected to the pressurized gas source, the breathing regulator generating a variable pressure drive gas and presenting a breathing gas intermediate the mouthpiece and the assisted breathing loop;
   (d) a variable volume chamber in the assisted breathing loop, the variable volume chamber fluidly connected to the breathing regulator to receive and provide breathing gas;
   (e) positioning means for varying a volume of the assisted breathing loop by varying a volume of the variable volume chamber in response to pressure changes of the variable pressure drive gas acting against a variable and position dependent force;

(f) a loop seal valve in the assisted breathing loop, the loop seal valve fluidly connected to the assisted breathing loop and selected to permit passing breathing gas one way from the assisted breathing loop into a surrounding environment in response to the variable pressure drive gas at a predetermined volume of breathing gas retained in the variable volume chamber; and (g) the breathing regulator controlling venting of the variable pressure drive gas back into the assisted breathing loop, the drive gas presented to fluid connections between the breathing regulator, the positioning means for varying the volume of the variable volume chamber, and the loop seal valve to control passing breathing gas from the assisted breathing loop to the surrounding environment.

2. The re-breathing device of claim 1, further comprising a loop make up valve, the loop make up valve selected to pass at least one of the pressurized gas and the drive gas into the assisted breathing loop in response to a given volume of the variable volume chamber.

3. The re-breathing device of claim 1, wherein the positioning means varies the volume of the variable volume chamber in response to a breathing pattern of the user.

4. The re-breathing device of claim 3, wherein the drive gas vented into the breathing loop has a sufficient quantity to provide for metabolic oxygen makeup needs without exceeding oxygen toxicity limits of the user.

5. The re-breathing device of claim 1, further comprising a first one way exhale valve in the assisted breathing loop fluidly intermediate the breathing regulator and the variable volume chamber for permitting one way flow of breathing gas from the breathing regulator to the variable volume chamber.

6. The re-breathing device of claim 1, further comprising a second one way exhale valve in the assisted breathing loop fluidly intermediate the breathing regulator and the variable volume chamber for permitting one way flow of breathing gas from the breathing regulator to the variable volume chamber.

7. The re-breathing device of claim 1, further comprising a first one way inhale valve in the assisted breathing loop for permitting one way flow of breathing gas in the assisted breathing loop to the breathing regulator.

8. The re-breathing device of claim 1, further comprising a second one way inhale valve in the assisted breathing loop for permitting one way flow of breathing gas in the assisted breathing loop to the breathing regulator.

9. The re-breathing device of claim 1, further comprising a bailout valve fluidly connected to the drive gas presented by the breathing regulator for selectively passing the drive gas to mix with breathing gas in the breathing regulator for direct breathing by the user and precluding passage of breathing gas from the assisted breathing loop to the breathing regulator.

10. The re-breathing device of claim 1, further comprising a decompression valve fluidly connected to a breathing regulator vent valve to vary a portion of venting drive gas between passing to the assisted breathing loop and passing from the assisted breathing loop.

11. The re-breathing device of claim 1, further comprising a high pressure metabolic gas storage bottle containing gas suitable for providing for the metabolic oxygen makeup needs of the user.

12. The re-breathing device of claim 11, further comprising a metabolic makeup gas dosing unit fluidly intermediate the high pressure metabolic gas storage bottle and the assisted breathing loop, the dosing unit being actuated by the drive gas.

13. The re-breathing device of claim 11, further comprising a relative humidity reducer fluidly intermediate the assisted breathing loop and one of the metabolic gas storage bottle, the pressurized gas source, and the regulator presented drive gas.

14. The re-breathing device of claim 1, wherein the positioning means includes a drive cylinder and drive piston.

15. The re-breathing device of claim 14, wherein a non-drive side of the drive piston is selected to expel water from the assisted breathing loop.

16. A method for providing a breathing gas to a user in a re-breathing device, the method comprising:

(a) supplying, via a breathing regulator, a variable pressure drive gas from a pressurized gas source to positioning means for changing a volume of an assisted breathing loop, the positioning means being responsive to the breathing pattern of the user; and (b) changing a volume of the assisted breathing loop in response to the positioning means to reduce an amount of work required for breathing from the assisted breathing loop.

17. The method of claim 16, further comprising urging a loop seal valve to a closed position until the volume of the assisted breathing loop is at a predetermined volume.

18. The method of claim 16, further comprising urging a loop seal valve to a closed position until the volume of the assisted breathing loop is at a maximum volume.

19. The method of claim 16, wherein the variable pressurize drive gas increases pressure to decrease the volume of the assisted breathing loop thereby forcibly assisting with inhalation by the user, and decreases pressure to increase the volume of the assisted breathing loop thereby forcibly assisting with exhalation by the user.

20. The method of claim 16, further comprising opening a make up valve upon the volume of the assisted breathing loop reaching a predetermined volume.

21. The method of claim 16, further comprising opening a make up valve in response to an insufficient volume of breathing gas in the assisted breathing loop for inhalation by the user.

22. The method of claim 16, further comprising venting a sufficient quantity of drive gas into the breathing loop to provide for metabolic oxygen makeup needs without exceeding oxygen toxicity limits of the user.

* * * * *